United States Patent
Hayes

(10) Patent No.: US 8,663,913 B2
(45) Date of Patent: Mar. 4, 2014

(54) PHAGE LAMBDA DISPLAY CONSTRUCTS

(76) Inventor: Sidney Hayes, Saskatoon (CA)

( * ) Notice: Subject to any disclaimer, the term of this patent is extended or adjusted under 35 U.S.C. 154(b) by 275 days.

(21) Appl. No.: 12/991,704

(22) PCT Filed: May 11, 2009

(86) PCT No.: PCT/CA2009/000603
§ 371 (c)(1),
(2), (4) Date: Jan. 4, 2011

(87) PCT Pub. No.: WO2009/135295
PCT Pub. Date: Nov. 12, 2009

(65) Prior Publication Data
US 2011/0092391 A1    Apr. 21, 2011

Related U.S. Application Data

(66) Substitute for application No. 61/051,712, filed on May 9, 2008.

(51) Int. Cl.
C12Q 1/68 (2006.01)
C12Q 1/70 (2006.01)
C12N 7/02 (2006.01)

(52) U.S. Cl.
USPC .............................. 435/5; 435/6.1; 435/239

(58) Field of Classification Search
None
See application file for complete search history.

(56) References Cited

FOREIGN PATENT DOCUMENTS

| WO | 03010199 | 2/2003 |
|---|---|---|
| WO | 03096969 | 11/2003 |
| WO | 2006058159 | 6/2006 |
| WO | WO2007/015704 | 2/2007 |
| WO | WO2007/076101 | 7/2007 |

OTHER PUBLICATIONS

Sternberg et al., Display of peptides and proteins on the surface of bacteriophage lamba, Proc. Natl. Acad. Sci. USA vol. 92, pp. 1609-1613, Feb. 1995, Genetics.*

Sternberg Nat et al: "Display of peptides and proteins on the surface of bacteriophage lambda", Proceedings of the National Academy of Sciences, National Academy of Sciences, US, vol. 92, No. 5, Jan. 1, 1995, pp. 1609-1613.

Santini C et al: "Efficient display of an HCV cDNA expression library as C-terminal fusion to the capsid protein D of bacteriophage lambda", Journal of Molecular Biology, Academic Press, United Kingdom, vol. 282, No. 1, Sep. 11, 1998, pp. 125-135.

Santi e et al: "Bacteriophage lambda display of complex cDNA libraries: a new approach to functional genomics", Journal of Molecular Biology, Academic Press, United Kingdom, vol. 296, No. 2, Feb. 19, 2000, pp. 497-508.

Gupta A et al: "High-density Functional Display of Proteins on Bacteriophage Lambda", Journal of Molecular Biology, Academic Press, United Kingdom, vol. 262, No. 1, Nov. 21, 2003, pp. 241-254.

(Continued)

Primary Examiner — Jim Ketter
Assistant Examiner — Reza Ghafoorian
(74) Attorney, Agent, or Firm — Ade & Company Inc; Michael R. William

(57) ABSTRACT

Bacteriophages in general and lambda phage in particular are powerful, flexible reagents who have yet to be exploited to their full potential. As discussed herein, the lambda phage head and/or genome comprises an easy to use and highly efficient delivery vehicle for delivering the expression products of a gene of interest systemically or to a particular tissue.

5 Claims, 2 Drawing Sheets atg act agt aaa gaa acc ttt acc cat tat cag ccg cag ggc aat agc gat ccg gcg cat acc gcg acc gcg ccg ggc ggc ctg agc gcg aaa gcg ccg gcg atg acc ccg ctg atg ctg gat acc agc agc cgt aaa ctg gtg gcg tgg gat ggc acc acc gat ggc gcg gcg gtg ggc att ctg gcg gtg gcg gcg gat cag acc agc acc acc ctg acc ttt tat aaa agc ggc acc ttt cgt tat gaa gat gtg ctg tgg ccg gaa gcg gcg agc gat gaa acc aaa aaa cgt acc gcg ttt gcg ggc acc gcg att tca att gtg

(56) References Cited

OTHER PUBLICATIONS

Mikawa Y G et al: "Surface Display of Proteins on Bacteriophage Lambda Heads", Journal of Molecular Biology, Academic Press, United Kingdom, vol. 262, No. 1, Jan. 1, 1996, pp. 21-30.

Forrer P et al: "High-level expression of soluble heterologous proteins in the cytoplasm of *Escherichia coli* by fusion to the bacteriophage lambda head protein D.", Gene Dec. 11, 1998, LNKD-PUBMED: 9931426, vol. 224, No. 1-2.

Eguchi A et al: "Protein transduction domain of HIV-I Tat protein promotes efficient delivery of DNA into mammalian cells", Journal of Biological Chemistry, American Society for Biochemistry and Molecular Biology, US, vol. 276, No. 28, Jul. 13, 2001, pp. 26204-26210.

Beghetto E et al: "Identification of a Human Immunodominant B-Cell Epitope within the GRA1 Antigen of *Toxoplasma gondii* by Phage Display of CDNA Libraries", International Journal of Parasitology, Pergamon Press, GB, vol. 31, No. 14, Dec. 1, 2001, pp. 1659-1668.

Mieschendahl, M. et al F-coded, temperature-sensitive lambda c1857 repressor gene for easy construction and regulation of lambda promoter-dependent pp. 1366-1369 ISSN 0021-9193, J Bacteriol. Dec. 1985; 164(3): 1366-1369.

Anderson L. et al; "DNA looping can enhance lysogenic CI transcription in phage lambda" Proceedings of the National Academy Sciences USA Apr. 15, 2008 vol. 105 pp. 5827-5832 ISSN 1091-6490.

* cited by examiner atg act agt aaa gaa acc ttt acc cat tat cag ccg cag ggc aat agc gat ccg gcg cat
acc gcg acc gcg ccg ggc ggc ctg agc gcg aaa gcg ccg gcg atg acc ccg ctg atg
ctg gat acc agc agc cgt aaa ctg gtg gcg tgg gat ggc acc acc gat ggc gcg gcg gtg
ggc att ctg gcg gtg gcg gcg gat cag acc agc acc acc ctg acc ttt tat aaa agc ggc
acc ttt cgt tat gaa gat gtg ctg tgg ccg gaa gcg gcg agc gat gaa acc aaa aaa cgt acc gcg ttt gcg ggc acc gcg att tca att gtg

Figure 1

TCTAGAtatc taacaccgtg cgtgttgact attttacctc tggcggtgat aatggttgcatgt

Figure 2

GGC GGC AGC GGC GCG CCG AGC TGG GCG GTG GAT ATG ATG CGT TTT AAT ATT AAT GAT TTT CTG CCG CCG GGC GGC GGC AGC AAT GCG GCG TAT CAG GGC GAT CGT GGC GTG GGC AGC AGC GCG GTG ATT CTG GAT GAT AAT TTT GTG ACC AAA GCG ACC GCG CTG ACC TAT GAT CCG TAT GTG AAT TAT AGC AGC GCG GCG TAT AGC CGT TAT TTT ACC CCG AAA CCG GTG CTG GAT AGC ACC ATT GAT TAT TTT CAG CCG AAT AAT AAA CGT AAT CAG CTG GCG GCG TAT GAT CAT GTG GGC CTG GGC ACC GCG TTT GAA AAT AGC ATT TAT TAA

Figure 3

CTCGaggaggAtCCATG

Figure 4

```
                                                      AvaI,SmlI  BstYI 78
         XbaI  ------EcoRV    oR2                oR1  XhoI,TliI  BamHI D     SpeI

TCTAGAtatc taacaccgtg cgtgttgact attttacctc tggcggtgat aatggttgca tgtCTCGagg agg AtCCatg actagtaaa
...tatc taacaccgtg cgtgttgact attttacctc tggcggtgat aatggttgca tgtactaagg aggttgt
```

Figure 5

```
          Modified timm self-terminator
          ----------------------------------------

XmaI
          SmaI                        ApoI  AccI
          ClaI  AvaI sites            EcoRI SalI
          --------------------        ----------------
TER
taatcgatcccgggtcagccccgggtttctttttgaattcgtgac
-------cccgg--tca---ccgggttttctt----------------

Lower line = bases in timm in common with lambda wild type
```

Figure 6

SEQUENCE LISTING

```
<160> NUMBER OF SEQ ID NOS: 7

<210> SEQ ID NO 1
<211> LENGTH: 330
<212> TYPE: DNA
<213> ORGANISM: artificial
<220> FEATURE:
<223> OTHER INFORMATION: synthetic codon-optomized lambda phage D-gene

<400> SEQUENCE: 1
atgactagta aagaaacctt tacccattat cagccgcagg gcaatagcga tccggcgcat      60
accgcgaccg cgccgggcgg cctgagcgcg aaagcgccgg cgatgacccc gctgatgctg     120
gataccagca gccgtaaact ggtggcgtgg gatggcacca ccgatggcgc ggcggtgggc     180
attctggcgg tggcggcgga tcagaccagc accaccctga cctttataa aagcggcacc     240 tttcgttatg aagatgtgct gtggccggaa gcggcgagcg atgaaaccaa aaaacgtacc     300
gcgtttgcgg gcaccgcgat ttcaattgtg                                      330

<210> SEQ ID NO 2
<211> LENGTH: 63
<212> TYPE: DNA
<213> ORGANISM: artificial
<220> FEATURE:
<223> OTHER INFORMATION: lambda pR promoter modified to include
      additional restriction enzyme sites

<400> SEQUENCE: 2
tctagatatc taacaccgtg cgtgttgact attttacctc tggcggtgat aatggttgca      60
tgt                                                                    63

<210> SEQ ID NO 3
<211> LENGTH: 336
<212> TYPE: DNA
<213> ORGANISM: artificial
<220> FEATURE:
<223> OTHER INFORMATION: artificial sequence encoding porcine
      circovirus2 cap protein epitopes separated by spacer sequences

<400> SEQUENCE: 3
ggcggcagcg gcgcgccgag ctgggcggtg gatatgatgc gttttaatat taatgatttt      60
ctgccgccgg gcggcggcag caatgcggcg tatcagggcg atcgtggcgt gggcagcagc     120
gcggtgattc tggatgataa ttttgtgacc aaagcgaccg cgctgaccta tgatccgtat     180
gtgaattata gcagcgcggc gtatagccgt tattttaccc cgaaaccggt gctggatagc     240
```

```
accattgatt attttcagcc gaataataaa cgtaatcagc tggcggcgta tgatcatgtg        300
ggcctgggca ccgcgtttga aaatagcatt tattaa                                  336
```

<210> SEQ ID NO 4
<211> LENGTH: 17
<212> TYPE: DNA
<213> ORGANISM: artificial
<220> FEATURE:
<223> OTHER INFORMATION: shine-delgano sequence modified to include
      BamHI site and flanking nucleotides

<400> SEQUENCE: 4

```
ctcgaggagg atccatg                                                       17
```

<210> SEQ ID NO 5
<211> LENGTH: 89
<212> TYPE: DNA
<213> ORGANISM: artificial
<220> FEATURE:
<223> OTHER INFORMATION: combination of seq id No 2 and seq id No. 4 -
      modified lambda pR promoter fused to modified Shine Delgano
      sequence

<400> SEQUENCE: 5

```
tctagatatc taacaccgtg cgtgttgact attttacctc tggcggtgat aatggttgca        60
tgtctcgagg aggatccatg actagtaaa                                          89
```

<210> SEQ ID NO 6
<211> LENGTH: 71
<212> TYPE: DNA
<213> ORGANISM: Bacteriophage lambda

<400> SEQUENCE: 6

```
tatctaacac cgtgcgtgtt gactatttta cctctggcgg tgataatggt tgcatgtact        60
aaggaggttg t                                                             71
```

<210> SEQ ID NO 7
<211> LENGTH: 47
<212> TYPE: DNA
<213> ORGANISM: artificial
<220> FEATURE:
<223> OTHER INFORMATION: modified lambda timm termination sequence

<400> SEQUENCE: 7

```
taatcgatcc cggggtcagc cccgggtttt cttttgaatt cgtcgac                      47
```

PHAGE LAMBDA DISPLAY CONSTRUCTS

PRIOR APPLICATION INFORMATION

The instant application claims the benefit of U.S. Provisional Patent Application 61/051,712, filed May 9, 2008.

BACKGROUND OF THE INVENTION

Phages are bacterial viruses. For example, lambda phage encapsulates a 48.5 kD duplex DNA in a capsid head of about 55 nm diameter. The genetics of lambda phage are well established and well understood. For example, the lambda D protein is a small protein (11.4 kDa) that acts to stabilize the lambda phage head or capsid but is dispensable for heads packaged with a DNA duplex less than 82% of the wild type lambda genome. As is well known to those of skill in the art, versions of lambda can be used as insertion or replacement vectors for cloning foreign DNA up to about 24 kilobase pairs (kbp).

Phages (in general), when administered to an animal rapidly circulate throughout the tissues of the animal and are removed from the circulation by the spleen, liver and filtering organs of the reticuloendothelial system (Geier et al., 1973, Nature 246: 221-223; Inchley, Clin Exp Immunol 5: 173-187; Keller and Engley, 1958, Proc Soc Exp Biol Med 98: 577-580). Phages have maintained viability for up to 2-3 weeks in spleen cells, indicating that they were neither neutralized by antibody nor engulfed by macrophages, but rather passively entrapped (sequestered). Viable phages have been detected in the circulation within 5 minutes of gastric delivery in mice, suggesting that significant numbers of phages can enter the circulation by diffusion, rather than via the lymphatic system (Keller and Engley, 1958). Phages delivered orally to rabbits were found in the blood plasma and most organs up to 4 days after administration, and persisted in the blood plasma and most organs up to 4 days after administration, and persisted in the spleen up to 12 days (Reynaud et al., 1992, Vet Microbiol 30: 203-212).

SUMMARY OF THE INVENTION

According to an aspect of the invention, there is provided a nucleic acid molecule encoding lambdaphage D gene having a nucleotide sequence as set forth in SEQ ID No. 1.

According to a further aspect of the invention, there is provided an expression system comprising a nucleic acid molecule comprising lambda pR promoter having a nucleotide sequence as set forth in SEQ ID No. 2 operably linked to a nucleic acid molecule encoding lambdaphage D gene having a nucleotide sequence as set forth in SEQ ID No. 1.

According to a further aspect of the invention, there is provided a method of preparing a recombinant lambda phage particle comprising:

providing a permissive host bacterial cell comprising an expression system comprising a nucleic acid molecule comprising lambda pR promoter having a nucleotide sequence as set forth in SEQ ID No. 2 operably linked to a nucleic acid molecule encoding lambdaphage D gene having a nucleotide sequence as set forth in SEQ ID No. 1, said lambdaphage D gene sequence having inserted in frame with the lambdaphage D gene a nucleic acid molecule encoding a gene of interest, said permissive host bacterial cell being suitable for vegetative growth of lambdaphage and further comprising the $cI^{TS}857$ repressor;

growing a plurality of cultures of said permissive host bacterial cell, each respective culture being grown at a temperature between 34-44° C.; and determining the number of phage particles produced in each respective culture, thereby determining the optimal temperature for phage assembly of a recombinant lambda phage particle expressing the gene of interest.

According to a further aspect of the invention, there is provided a method of preparing a recombinant lambda phage particle comprising:

providing a permissive host bacterial cell comprising:
an expression system comprising a nucleic acid molecule comprising lambda pR promoter having a nucleotide sequence as set forth in SEQ ID No. 2 operably linked to a nucleic acid molecule encoding lambdaphage D gene having a nucleotide sequence as set forth in SEQ ID No. 1, said lambdaphage D gene sequence having inserted in frame with the lambdaphage D gene a nucleic acid molecule encoding a first gene of interest; and
lambdaphage genomic DNA comprising a eukaryotic promoter operably linked to a second gene of interest;

growing a culture of said permissive host bacterial cell under conditions suitable for vegetative growth of lambda bacteriophage, thereby producing a recombinant lambdaphage particle having a particle comprising the gene product of the first gene of interest on an exterior of the particle and a DNA molecule arranged to express the second gene of interest.

According to another aspect of the invention, there is provided a method of preparing a recombinant lambda phage particle library comprising:

providing a permissive host bacterial cell comprising:
an expression system comprising a nucleic acid molecule comprising lambda pR promoter having a nucleotide sequence as set forth in SEQ ID No. 2 operably linked to a nucleic acid molecule encoding lambdaphage D gene having a nucleotide sequence as set forth in SEQ ID No. 1;
$cI^{TS}857$ repressor; and
a lysogenic lambdaphage inserted within the genomic DNA of the permissive host bacterial cell;

incubating a culture of the permissive host bacterial cell at 42° C. for a period of time suitable to induce expression of exo-bet-gam;

incubating the culture at 30° C.;

transforming the culture with a plurality of single stranded nucleic acid molecules comprising 15 to 54 random nucleotides having at either end sufficient DNA homologous to the expression system to initiate a crossover event between the single-stranded nucleic acid molecule and the nucleic acid molecule encoding the expression system such that the random nucleotides are inserted into the region of the lambdaphage D-gene encoding the N-terminal region of the gene product;

allowing crossover events to occur;

shifting the culture to a temperature between 34-42° C., thereby inducing the lambdaphage; and recovering the lambdaphage particles from the culture.

According to a further aspect of the invention, there is provided an expression system comprising a nucleic acid molecule comprising lambda pR promoter having a nucleotide sequence as set forth in SEQ ID No. 2 operably linked to a nucleic acid molecule encoding a Shine-Delgarno sequence as set forth in SEQ ID No. 4.

BRIEF DESCRIPTION OF THE DRAWINGS

FIG. 1. Sequence of codon-optimized D gene (SEQ ID No. 1).

FIG. 2. Lambda pR promoter/operator sequence (SEQ ID No. 2).

FIG. 3. Sequence of four fused synthetic epitopes of porcine circovirus 2 capsid protein (SEQ ID No. 3).

FIG. 4. Modified Shine-Delgarno sequence (SEQ ID No. 4)

FIG. 5. Modified Lambda pR/Shine Delgarno sequence (SEQ ID No. 5) (upper frame). Wild type sequence is shown in lower frame (SEQ ID No. 6).

FIG. 6. Modified Lambda timm termination signal (SEQ ID NO. 7).

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Bacteriophages in general and lambda phage in particular are powerful, flexible reagents who have yet to be exploited to their full potential. As discussed herein, the lambda phage head comprises an easy to use and highly efficient delivery vehicle for delivering the expression products of a gene of interest systemically or to a particular tissue.

Described herein is a system for phage display wherein the expression products of gene(s) of interest are delivered using a lambda phage particle. Also described are methods for preparing these reagents and components of the system used to exploit this invention.

Specifically, as described herein, there is provided a nucleic acid molecule encoding lambdaphage D gene having a nucleotide sequence as set forth in SEQ ID No. 1.

In another embodiment of the invention, there is provided an expression system comprising a nucleic acid molecule comprising lambda pR promoter having a nucleotide sequence as set forth in SEQ ID No. 2 operably linked to a nucleic acid molecule encoding lambdaphage D gene having a nucleotide sequence as set forth in SEQ ID No. 1. As will be apparent to one of skill in the art, 'operably linked' refers to the fact that under proper conditions, expression of the modified D gene is driven by the lambda promoter, as discussed below.

In another aspect of the invention, there is provided a method of preparing a lambda phage particle comprising: providing a permissive host bacterial cell comprising an expression system comprising a nucleic acid molecule comprising lambda pR promoter having a nucleotide sequence as set forth in SEQ ID No. 2, operably linked to a nucleic acid molecule encoding a Shine-Delgarno sequence as set forth in SEQ ID No. 4, operably linked to a nucleic acid molecule encoding lambdaphage D gene having a nucleotide sequence as set forth in SEQ ID No. 1, said lambdaphage D gene sequence having inserted in frame with the lambdaphage D gene a nucleic acid molecule encoding a gene of interest, said permissive host bacterial cell being suitable for vegetative growth of lambdaphage and further comprising the $cI^{TS}857$ repressor; growing a plurality of cultures of said permissive host bacterial cell, each respective culture being grown at a temperature between 25-44° C.; and determining the number of phage particles produced in each respective culture, thereby determining the optimal temperature for phage assembly of a recombinant lambda phage particle displaying the gene of interest. In this manner, display phage particle assembly can be quickly and easily optimized regardless of the size and/or nature of the fusion insert simply by varying temperature and determining the temperature that produces the best yield size using any of a variety of means known in the art.

In other embodiments, there is provided a method of preparing a lambda phage particle comprising: providing a permissive host bacterial cell comprising: an expression system comprising a nucleic acid molecule comprising lambda pR promoter having a nucleotide sequence as set forth in SEQ ID No. 2 operably linked to a nucleic acid molecule encoding lambdaphage D gene having a nucleotide sequence as set forth in SEQ ID No. 1, said lambdaphage D gene sequence having inserted in frame with the lambdaphage D gene a nucleic acid molecule encoding a first gene of interest; and lambdaphage genomic DNA comprising a eukaryotic promoter operably linked to a second gene of interest; growing a culture of said permissive host bacterial cell under conditions suitable for vegetative growth of lambda bacteriophage, thereby producing a recombinant lambdaphage particle having a particle comprising the gene product of the first gene of interest on an exterior of the particle and a DNA molecule arranged to express the second gene of interest. In this manner, lambda display-DNA particles having a particle displaying the first gene of interest on the surface of the particle and a second gene of interest suitable for expression in a eukaryotic cell within the genome of the packaged lambda DNA can be produced, as discussed below.

In other aspects of the invention, there are provided methods of preparing a recombinant lambda phage particle library comprising: providing a permissive host bacterial cell comprising: an expression system comprising a nucleic acid molecule comprising lambda pR promoter having a nucleotide sequence as set forth in SEQ ID No. 2 operably linked to a nucleic acid molecule encoding lambdaphage D gene having a nucleotide sequence as set forth in SEQ ID No. 1; $cI^{TS}857$ repressor; and a lysogenic lambdaphage inserted within the genomic DNA of the permissive host bacterial cell; incubating a culture of the permissive host bacterial cell at 42° C. for a period of time suitable to induce expression of exo-bet-gam; incubating the culture at 30° C.; transforming the culture with a plurality of single stranded nucleic acid molecules comprising 15 to 54 random nucleotides having at either end sufficient DNA homologous to the expression system to initiate a crossover event between the single-stranded nucleic acid molecule and the nucleic acid molecule encoding the expression system such that the random nucleotides are inserted into the region of the lambdaphage D-gene encoding the N-terminal region of the gene product; allowing crossover events to occur; shifting the culture to a temperature between 34-42° C., thereby inducing the lambdaphage; and recovering the lambdaphage particles from the culture.

According to another aspect of the invention, there is provided a method of preparing a composition comprising: growing a suitable host bacterial cell comprising an inducible heteroimmune lambdoid phage that is defective for cell lysis and phage burst to a suitable culture density; inducing the prophage such that mature phage particles are produced within the bacterial cell; concentrating the cells; and treating the cells with killed vaccine preparation agents, thereby producing a composition. As will be appreciated by one of skill in the art, such a composition may be used to induce or elicit an immune response from a patient.

According to a further aspect of the invention, there is provided a method of preparing bacteriophage comprising: growing a suitable host bacterial cell comprising an inducible heteroimmune lambdoid phage that has a cannot bind or attach to the host bacterial cell and is unable to lyse the host bacterial cell to a suitable culture density; inducing the prophage such that mature phage particles are produced within the bacterial cell; lysing the cells; and recovering the unbound phage particles from the culture. As discussed below, this method can be used to produce higher titers of bacteriophage in a much more efficient manner.

In another aspect of the invention, there is provided a method of preparing a lambda phage particles comprising: providing a permissive host bacterial cell comprising an expression system comprising a nucleic acid molecule comprising lambda pR promoter having a nucleotide sequence as set forth in SEQ ID No. 2 operably linked to a nucleic acid molecule as set forth in SEQ ID No. 4, operably linked to a functional lambda phage gene, said permissive host bacterial cell being suitable for vegetative growth of lambdaphage and further comprising the cl$^{TS}$857 repressor with the proviso that the lambdaphage gene is deleted from the phage genome; subjecting the host bacterial cell to conditions such that bacteriophage particle assembly is initiated; and recovering the bacteriophage particles from the culture, thereby providing a recombinant lambdaphage particle but said particles lacking a functioning copy of the essential lambdaphage gene.

In another aspect of the invention, there is provided an cl857[Ts]-pR-GOI-timm expression system operably linked to the lambdaphage cl857[Ts] repressor gene and comprising a nucleic acid molecule as set forth in SEQ ID No. 5 comprising lambda pR promoter having a nucleotide sequence as set forth in SEQ ID No. 2 operably linked to a nucleic acid molecule encoding a Shine-Delgarno sequence as set forth in SEQ ID No. 4, operably linked to a nucleic acid molecule encoding a gene of interest, operably linked to a modified Rho-independent mRNA termination signal timm set forth in SEQ ID No. 7. The expression system comprises, in order, a nucleic acid molecule comprising lambda pR promoter having a nucleotide sequence as set forth in SEQ ID No. 2 operably linked to a nucleic acid molecule encoding a Shine-Delgarno sequence as set forth in SEQ ID No. 4, operably linked to a nucleic acid molecule encoding a gene of interest, operably linked to a modified Rho-independent mRNA termination signal timm set forth in SEQ ID No. 7. Thus, transcription of the gene of interest is driven by the pR promoter and is controlled by the cl857[Ts] (temperature-sensitive) repressor. This transcription is terminated by the timm termination sequence as discussed herein. In addition, the gene of interest is fused downstream of the modified Shine-Delgarno sequence, meaning that high levels of transcription of the gene of interest can be easily induced and the transcripts will be efficiently translated, as discussed herein.

As will be appreciated by one of skill in the art, and as discussed herein, SEQ ID No. 5 and FIG. 5 comprises the modified pR promoter shown in SEQ ID No. 2 and FIG. 2 fused to the Shine-Delgano sequence shown in SEQ ID No. 4 and shown in FIG. 4. As such, it is to be understood that in some embodiments of the invention, the nucleotide sequence as set forth in SEQ ID No. 5 may be substituted for nucleotide sequences comprising both SEQ ID No. 2 and SEQ ID No. 4.

As discussed below, the strategy of phage lambda display is distinct from phage therapy in that phage lambda display reagents can be fully incapacitated (genetically and/or mechanically) to prevent phage growth following infection of a host. Described herein are a number of reagents for use within a phage lambda particle preparation process system, including suitable host cells, phage assembly vectors and the like.

There are multiple potential applications for phage display agents. Exemplary examples include but are by no means limited to: alternatives (substitutes) for antibiotics; as display vehicles in targeted gene delivery; as medical diagnostic aids; for the isolation of tissue-specific peptides; for use as tissue imaging agents both within and outside an animal; for cell targeting; for studying the specificities of immune responses of patients with various diseases; for cancer therapy; for use in autoimmune disorders and age-related conditions; for use as vaccines and antisera; for use as biodetectors for a variety of biological threat agents (viruses, bacteria, spores, toxins); for use in drug and vaccine delivery to specific cells; and for use in applications involving surface display vehicles functioning as biocatalysts or for bioadsorption.

A particle preparation process was developed for making lambda display particles (LDP) lambda DNA particles (LDNAP) (DNA vaccines delivered in phage particle) and lambda display-DNA particles ((L2DP) DNA vaccines delivered in surface-display phage particle with cell targeting property) with utility as surface display agents and vaccines, which include features contributing to environmental safety and limiting reverse engineering. As discussed below, in these constructs, many of the genes of interest are expressed as a fusion with a codon optimized D-gene (SEQ ID No. 1).

Lambda display particle are surface display vehicles, lambda DNA particles have primary use as DNA vaccines delivered in a phage particle and are not coated with a fusion protein, and the lambda display-DNA particles are DNA particle vaccines with independent surface display permitting targeted vaccine delivery to particular cells. In one embodiment, a lambda display particle vaccine displaying four immunorelevant epitopes of the porcine circovirus 2 capsid protein has been prepared and is described below. The 110 amino acids derived from codon optimized D protein are followed by spacer sequence and then the synthetic cap sequence (codon optimized for E. coli) epitopes representing amino acids 65-87, 113-146, 158-183, and 194-207 (each segment separated by spacer sequences). The sequence is shown in FIG. 3 (SEQ ID No. 3).

The lambda display particle, lambda DNA particles, lambda display-DNA particles reagents differ from conventional phage therapy reagents in that they are not designed to infect and then lyse/kill targeted bacterial cells. Nevertheless, they can be used as antimicrobial agents because of engineered properties for i) targeting and killing bacterial pathogens (omitting infection and cell lysis); ii) bioadsorption of elaborated toxin(s) or iii) for targeting macrophages (or other target eukaryotic cells) for uptake and internal eukaryotic expression of phage-vector-encoded antibacterial/antimetabolic substance(s).

Lambda display particle are surface display vehicles with potential use as i) vaccines, ii) antibody substitutes, e.g. as antidotes, antitoxins and antisera, iii) as anti-microbial agents, and iv) and in combination with phage particle DNA vaccines (lambda DNA particles) to make lambda display-DNA particles.

Some examples of potential utility of the lambda display particle and lambda display-DNA particles surface display vehicles include but are by no means limited to i) for therapeutic vaccine peptide display (as vaccines); ii) antidotes (antibody/antisera substitutes: e.g., as antitoxins); iii) targeted gene/cell delivery: of therapeutic anti-metabolites (e.g. delivery of an expression system that expresses an inhibitor RNA blocking some aspect of cell metabolism); isolation of tissue-specific peptides/proteins; tissue imaging agents (in vitro and in vivo); studying the specificities of immune responses of patients with various diseases; cancer therapy, autoimmune and age-related disorders/conditions; diagnostic assays; as biodetectors for a variety of threat agents (viruses, bacteria, spores, toxins); as biocatalysts or for bioadsorption; and iv) anti-microbial agents for drug/vaccine/targeting agent delivery to specific cells.

As discussed herein, a lambda display particle can be prepared by either: a) expression of D-fusion gene construct on plasmid or b) expression of genes placed in the *E. coli* chromosome within cryptic defective prophage and regulated by cI[Ts]857 repressor.

To make a lambda display particle, infect *E. coli* cells capable of expressing D-GOI fusion protein with genetically modified lambda phage. For example, to make D-CAP coated lambda display particle, infect any one of the following cells *E. coli*[p27789646], *E. coli*[pclpR-D-CAP-timm] or *E. coli*:: D-CAP fusion cell, with lambda variant. As will be apparent to one of skill in the art, other suitable strains may be used within the invention and the examples provided herein are for illustrative purposes only.

For example, 22 plasmid constructs and chromosomally engineered *E. coli* cells described below (i.e., cells with any of the 22 pclpR-based plasmids, and the D-cells, D-gene-of-interest-fusion cells, and gene-of-interest fusion cells) were custom designed and constructed for the purpose of preparing lambda display particles that do not genetically encode the information being displayed. These potential vaccines/reagents cannot be reverse engineered. In designing this process, two model system processes were developed involving: a) synthetic preparation of fused epitopes of a porcine circovirus 2 (PCV2) capsid gene; and b) development of a chromosomally engineered D-fusion cell and variations.

Specifically, the exemplary plasmids for the process are:
1) p27789648=pR-D-CAP-timm, which was used for initial lambda display particle PCV2 vaccine;
2) p27789646-clpR, which is used for making N-terminal D-fusions;
3) pRλcl857-I/II-D-CAP=timm, which is used for making N-terminal D-fusions;
4) pclpR;
5) pclpR-D-CAP-timm which is used for controlling display concentration of fusion protein on lambda display particles, as described herein;
6) pclpR-D-SPA-timm—SPA is a dual, cleavable, protein affinity tag, used for identification and characterization of the cellular interactions of designed gene fusion proteins;
7) pclpR-D-GOI-timm, which is used for making vaccine/reagent displaying any fused gene of interest on lambda display particles;
8) pclpR-D-GOI-SPA-timm (two versions);
9) pclpR-GOI-timm;
10) pclpR-GOI-SPA-timm;
11) pclpR-D-CAP-timm-Kan;
12) pclpR-D-SPA-timm-Kan;
13) pclpR-D-GOI-timm-Kan;
14) pclpR-D-GOI-SPA-timm-Kan;
15) pclpR-GOI-timm-Kan; and
16) pclpR-GOI-SPA-timm-Kan.
17) pclpR-D-CAP-timm-Kan-ninA;
18) pclpR-D-SPA-timm-Kan-ninA;
19) pclpR-D-GOI-timm-Kan-ninA;
20) pclpR-D-GOI-SPA-timm-Kan-ninA;
21) pclpR-GOI-timm-Kan-ninA; and
22) pclpR-GOI-SPA-timm-Kan-ninA.

The exemplary cells for the process are:
1) D-cell;
2) D-CAP-fusion cell;
3) D-GOI-fusion cell;
4) D-SPA-fusion cell;
5) D-GOI-SPA-fusion cell;
6) GOI-fusion cell; and
7) GOI-SPA-fusion cell.
8) LDP-LDNAP-L2DP-cells
9) LDP-LDNAP-L2DP-exclusion cells Lambda DNA particles are primarily used as DNA vaccines delivered in phage particle. The lambda DNA particles are not coated with D-fusion protein. Lambda DNA particles are simply grown in permissive *E. coli* cells.

As per above, 6 exemplary plasmids are described below, and were custom designed and constructed for the purpose of preparing lambda DNA particles for the purpose of placing a eukaryotic expression cassette for a vaccine gene into a bacteriophage lambda DNA cloning vector that was optimized for safety (discussed below). In designing this process, a model system process was developed that includes: a) incorporation of porcine circovirus 2 capsid gene into mammalian expression cassette, which was in turn cloned into lambda cloning vector, modified by our design.

The five plasmids pSJH-A through pSJH-E represent versions of a designer plasmid constructed for use in preparing lambda DNA particles. All current versions (A-E) of these plasmids include a eukaryotic promoter [CMV] and polyadenylation signal [BGHPA or SV40PA] cloned within designer plasmid pSJH, containing synthetically incorporated special features. As will be apparent to one of skill in the art, the eukaryotic cytomegalovirus promoter is one of many possible choices that work well in most eukaryotic cells. Other examples that could be substituted for the CMV promoter include an RSV promoter or SV40 promoter which have equally strong activity in a broad variety of eukaryotic cells.

In each version of pSJH, the gene (or gene fragment) of interest is cloned between the eukaryotic-promoter-intron sequence [INT] and the polyadenylation signal. Some of the plasmids include chromosomal insulator [INS] sequences placed before the promoter and after the polyadenylation sequence, as discussed below. These plasmids each have specially designed multiple cloning sites (MAC) and have been engineered to eliminate any prokaryotic promoters within the eukaryotic expression unit. The eukaryotic expression unit was designed to be directly removed from a pSJH[version] and directly cloned into specially modified (for safety) bacteriophage lambda DNA, and PFU are selected as lambda DNA particles on special bacterial cells. The lambda DNA particles include safety features designed to prevent multiplication of the phage within the natural environment, and the lambda DNA particles are devoid of antibiotic resistance markers and do not use commercially available plasmids or phages.

The exemplary plasmids described above for the lambda DNA particles process are:
pSJH-A: INS-CMV-INT-MCS-BGHPA-INS;
pSJH-B: INS-CMV-INT-MCS-SV40PA;
pSJH-C: CMV-INT-MCS-BGHPA-INS;
pSJH-D: CMV-INT-MCS-SV40PA;
pSJH-D': CMV-INT-MCS-SV40DNA;
pSJH-E: CMV-INT-MCS-SV40PA-φfi-SV40ori; and
pSJH-[version]-GOI, for example: pSJH-D'-PCV2CAP, which is the developmental lambda DNA particle model system used to express Orf2 CAP protein for PCV2 virus from phage lambda variant.

In the above-described plasmids, the MCS was designed as AscI-XhoI-NotI-ClaI, where AscI and NotI have rare 8 bp target sites, and the ClaI site adjacent to SV40PA does not have an adjacent "C", so that there is no GATC Dam methylation to inhibit ClaI restriction endonuclease. In addition the restriction sites straddling the eukaryotic cassette are, for example: EcoRI-SstI-KpnI-BglII--[eukaryotic cassette]--BsiWI-XbaI, although other suitable restriction enzymes and arrangements may be used as will be appreciated by one of skill in the art.

Plasmid pSJH-[version]-Gene-Of-Interest is prepared by cloning a PCR amplification of the gene of interest into the MCS of one of the pSJH versions. One of the advantages of the pSJH plasmids is that they encode unique restriction sites engineered into the outer boundaries of the eukaryotic expression cassette that enable it to be removed and directly cloned into the lambda cloning vector, as discussed below.

The plasmids versions A-E of pSJH can be used to clone the gene of interest. The genetic material encoding the gene of interest is preferably codon optimized and is first moved into a specially designed MCS in one of the designer plasmids described above, e.g., pSJH-D', downstream of powerful eukaryotic promoter-intron combination and upstream of eukaryotic polyadenylation signal to make pSJH-D'-gene of interest. For example, plasmid pSJH-D' includes selected parts but not the entire expression region of the mammalian expression vector pCI-neo. This vector has been shown to give high expression when transformed into eukaryotic cells. In version pSJH-E, the SV40 origin is incorporated so that the segment is able to replicate within a eukaryotic cell. In some embodiments, pSJH-E may be used to make a more powerful, but less controllable lambda DNA particles.

Plasmid versions B, D and E of pSJH encode the SV40-PA (polyadenylation signal), whereas versions A and C have the BGH-PA (bovine growth hormone polyadenylation signal). The BGH-PA sequence does not include a MfeI restriction target site, which is present in SV40-PA, and necessitated the EcoRI end (rather than Mfe-ends) for the eukaryotic expression cassette in versions B, D and E. In plasmid pSJH-A the eukaryotic expression cassette is straddled by "insulator" (INS) sequences, while plasmid pSJH-C has a eukaryotic insulator sequence downstream of the BGH-PA sequence. An insulator is a sequence that prevents an activating or inactivating effect passing from one site to the other. The plasmids pSJH-A, pSJH-B and pSJH-C have eukaryotic expression cassettes that were derived from plasmid pMZS3F, which itself is derived from pCI-neo. All of the plasmids include an intron (INT) derived from plasmid pCI-neo, that is positioned between the CMV promoter and the MCS. The intron was included because studies have shown that if introns are deleted from a gene, its RNA product is exported much more slowly to the cytoplasm. This suggests that the intron may provide a signal for attachment of the export apparatus.

It is of note that in all of the pSJH plasmids, the bacterial T7 and T3 promoters present in pCI-neo and pMZS3F were genetically removed so that they would not interfere in eukaryotic cells with gene expression downstream from the eukaryotic promoter, or when a given plasmid is grown in *E. coli*.

Lambda display-DNA particles are DNA particle vaccines with independent surface display permitting targeted vaccine delivery to particular cells. Potential uses of these DNA particle-surface display vehicles include use as vaccines that are targeted to bind and be taken up by specific cells, and as cell targeting particles that deliver an interfering gene(s) into target cells to direct/interfere with cell metabolism or cell division/growth.

As will be known to those of skill in the art, lambda phage assembly will also tolerate the insertion of foreign DNA within its genome. This fact allows for the construction of powerful therapeutics, as discussed herein. For example, a system can be constructed wherein a peptide(s)/protein(s) that is not displayed from the lambda capsid can be expressed from the lambda display-DNA particles phage genome. In this instance a cloned eukaryotic expression cassette is inserted within the genome of the phage DNA packaged in the phage particle. When the particle is taken up by a eukaryotic cell the promoter on the eukaryotic expression cassette is recognized and the downstream peptide(s)/protein(s) of interest are expressed in the cell taking up the particle. As an example, ten or more different immunorelevant 22 amino acid domains of different influenza variants (avian, swine, human, etc) of a target protein can be expressed from one particle. In another example, the displayed peptide of interest could be an antibiotic such that the phage particles present an initial 'dose' of the antibiotic while a secondary 'dose' is provided by the expression cassette. Thus, in preferred embodiments, the lambda display-DNA particles comprise a first gene of interest which is expressed as a fusion with the lambda D gene such that the first gene of interest is presented on the capsid of the phage particle which is functionally related to a second gene of interest which is encoded within the lambda phage genomic DNA packaged inside the lambda phage particle. That is, the L2DP particle is coated by a first gene of interest fused with the lambda D gene. A second gene of interest is inserted on a eukaryotic expression cassette and is encoded within the phage genome. As discussed herein, the first gene of interest and the second gene of interest may be functionally related in that they encode the same or a functionally similar peptide (for example but by no means limited to an antibiotic or an antigenic epitope) or the first gene of interest may encode a targeting peptide to direct the particle to a specific location while the second gene of interest encodes an agent which will have a beneficial or therapeutic effect at that location. In other embodiments, the displayed D-fusion may be unrelated to the peptide expressed by the expression cassette, for example, the 'D-fusion' may be a targeting molecule, for example a receptor binding protein or other ligand which targets the transgenic particle to a particular tissue or cell type for subsequent expression of the peptide encoded in the expression cassette. In some embodiments, this peptide may induce or interfere with cell metabolism, cell division and/or cell growth, or the DNA sequence encoding the "peptide" would be replaced with a gene encoding an interfering RNA (iRNA).

In other embodiments, the gene to be expressed is operably linked to a suitable eukaryotic promoter and the expression cassette is inserted into the lambda genome. The lambda phage particle containing the expression cassette is then assembled through the use of helper phage genes as known in the art and the recombinant phage particles comprising the expression cassette are recovered and purified. As will be appreciated by one of skill in the art, there are numerous potential uses for particles such as these depending on the nature of the gene-of-interest within the expression cassette. For example, the gene-of-interest may encode an antigen or epitope for use in vaccination or may comprise a therapeutic peptide. In some embodiments, the promoter may comprise a strong, constitutive promoter (so that expression is 'on'), an inducible promoter (so that expression occurs when certain conditions are met) or a cell-specific promoter (so that expression occurs only in a specific location or subset of locations (tissues)). The expression cassette may further include for example a polyadenylation signal, an enhancer sequence, a eukaryotic origin of replication as well as other elements known in the art for promoting eukaryotic gene expression. Preferably, in these embodiments, the vaccine comprises a natural lambda particle that neither encodes nor displays fusion proteins.

The methods for preparing lambda display-DNA particles are similar for lambda display particles by either: a) expression of D-fusion gene construct on plasmid, or b) expression of genes placed in the *E. coli* chromosome within cryptic defective prophage and regulated by cI[Ts]857 repressor.

To make lambda display-DNA particles, infect *E. coli* cells capable of expressing D-GOI fusion protein with lambda DNA particle phage. For example, to make D-CAP coated lambda display-DNA particles, infect any one of the following cells *E. coli*[p27789646], *E. coli*[pclpR-D-CAP-timm] or *E. coli*::D-CAP fusion cell, with lambda DNA particle variant.

Phage Production and Safety Engineering Considerations:

LAMBDA DISPLAY PARTICLE—general preparations: In theory, any lambda phage or phage DNA hybrid that employs the decoration protein D encoded by lambda gene D (or a similar decoration protein from another lambdoid phage) can be used to prepare lambda display particles. All that is required is that the phage is able to grow vegetatively (produce a good burst) in cells expressing the D-gene-of-interest gene fusion from a plasmid or in a cell in which the D-gene-of-interest gene fusion is placed within the bacterial chromosome. The D-gene-of-interest fusion protein will compete with normal D protein for placement on the lambda head (capsid). The advantages of this method over cloning the D-gene-of-interest gene fusion within the phage genome include: a) prevents reverse engineering of the lambda display particle; b) the LPD particle is safe because release of the LPD particles within the environment does not reproduce the D-gene-of-interest gene fusion. Infection of naturally occurring *E. coli* cells produces normal lambda virus particles, which exist naturally within the environment; and c) both the plasmids expressing D-gene-of-interest and the D-gene-of-interest-fusion cells do not share any DNA homology to regions on the phage that straddle gene D. Therefore, the possibility of recombining the D-gene-of-interest into the infecting phage producing a phage genome that now encodes the D-GOI within the phage genome is essentially nill. This increases safety from both the reverse engineering and from the environmental release standpoint.

The system developed for making a lambda DNA particle vaccine for PCV2 expression in pigs is as follows. The phage vector was derived from a non-commercial vector, lambda Δb189 ΔKH54 BW1 Δnin5 QSR80. This vector forms large plaques, gives high titers with LB medium into $10^{11}$ pfu per ml, carries no antibiotic resistance marker(s), is deleted for most all of the immunity region (cI-rex) and thus cannot lysogenize infected cells, is deleted for the nin5 region so that it does not have recombination genes that are involved in the 'kleptomania' phenotype (steals genes from host: Genetics 170:1485-1499), has gene gam, so that it protects linear concatemeric-packagable-DNA formed via rolling circle replication, has a substitution of the lambda bor gene, will be deleted for lambda lom gene and int-xis-exo genes when used as a replacement vector (so it lacks both general recombination and site specific recombination genes and won't recombine into host chromosome), carries no bacterial genes, can be used as a insertion vector (accepting from 0 to about 4000 bp), can be used as a replacement vector (accepting from "0" to about 8000 bp). Optional features built into versions of this vector incapacitate it for either replication or capsid formation, neither being suppressible (except by growth on specially engineered cells) or revertable. In one embodiment of this phage vector, a promoter-green-fluorescent-protein (GFP) gene is cloned between the single EcoRI and single BsiWI sites. The eukaryotic expression cassette with EcoRI and BsiWI ends replaces the promoter-GFP gene segment and recombinant phage carrying the eukaryotic expression vector are selected that have lost promoter-GFP by examining for phage plaques that do not fluoresce under ultraviolet light.

The CMV-gene-of-interest-PA eukaryotic expression cassette is removed from pSJH-D-gene of interest by restriction digestion (depending upon internal gene of interest sequence). Typically, this is expected to be by cutting at EcoRI and at BsiWI or at Xba I sites, as shown in one version below:

EcoRI-SstI-KpnI-BglII--[eukaryotic cassette]--BsiWI--XbaI sequence

Alternatively, the eukaryotic expression cassette can be amplified by PCR if there is a problem digesting the fragment with EcoRI and BsiWI or XbaI, using special universal primers with homology to regions of pSJH-[version A-E] outside of the CMV-gene of interest-PA sequence.

Either the PCR or restriction fragment can then be cloned into one of two distinct insertion sites in the phage vector, for example, EcoRi or BsiWI sites, or between both insertion sites when the lambda genome is used as a replacement vector. Opposing primers flanking the MCS are used to sequence the CMV-gene of interest-PA using plaque PCR for both identification of correct insertion and the DNA sequence.

Vaccine/Reagent Production and Safety Engineering Considerations. Preventing Phage Particles Released into Environment from Multiplying.

It has been noted by empirical observation that highly dense, CsCl-banded phage preparations lose titer by a million- to trillion-fold (or more) when held refrigerated for years at 2-4° C. Nevertheless, these preparations retain equivalent A260 absorbance values as when initially banded. It is possible to use A260 absorbance values to determine phage particle numbers (live or dead) in calculating phage vaccine/reagent dosage for administration. Based upon this observation, it is possible to extrapolate that chemical or physical methods can be used to inactivate phages. However, we imagine several possible adverse effects (see below, methods 1-3). Therefore, we have focused on developing genetic strategies for inactivating phage multiplicity (methods 4 and 5).

1) Chemical treatments: Treatments like EDTA will reduce the titer by $10^3$-$10^5$, but result in popping the phage head. Use of chemical treatments to inactivate the phage particles is contra-indicated because residue/retention of the chemical can be transferred when the killed particles are administered. Use of toxic DNA damaging agents (genotoxins) may influence gene expression from lambda DNA particles or lambda display-DNA particles. Use of protein conformation or denaturing agents can influence peptide display from lambda display particles or lambda display-DNA particles.

2.) Radiation damage: Treatments, like ultraviolet irradiation, that crosslink DNA are contraindicated because they can significantly influence gene expression from lambda DNA particles and lambda display-DNA particles, and UV-treated genomes can be repaired when injected into host cells (Weigle reactivation).

3.) Heat can be used to inactivate phage particles; however, it is contra-indicated for lambda display particle and lambda display-DNA particles because of the potential denaturing effect on displayed fusion proteins.

4.) Only permit phage maturation or multiplication in fusion cells. The fusion-cells will supply an inducible, essential phage-function(s) to an infecting phage whose genome is defective (or deleted) for the function provided by the fusion cell. The fusion cells are prepared as described for D-cells. It is of note that suitable strains and plasmids for this process are described above.

4a) Incorporate several nonsense mutations into the vaccine/reagent phage. This method was used to make "safe" lambda cloning vectors, e.g., incorporation of Wam403 (involved in joining phage tail to capsid) and Eam1100 (major head protein) into the phage genome, as in vector λgt wesλB (Science, 1977, 196:175), but there are several disadvantages. The mutations are revertable at a measurable frequency (which is a special problem when preparing very high phage titer lysates and concentrating the phage) and the revertants, or sus+ recombinants can grow better and enrich themselves during phage propagation. The phage that escape from the laboratory condition can grow on natural suppressor strains within the environment and human gut, and since nonsense suppression is usually inefficient (5-10% or less) the yield of progeny phage being produced during vaccine/reagent preparation is reduced. In a further preferred embodiment, an insertion vector is prepared which includes a disruption within D such that stop codons are generated in all three reading frames. As will be appreciated by one of skill in the art, many different strategies may be used to disrupt translation of D so that only a recombinant event within D will allow expression of D. It is of note that while a single disruption of the D open reading frame need only be used, the advantage of preparing a disruption in all three reading frames is that expression of D as a result of suppressive frame-shifts are eliminated.

4b) Incorporate an engineered deletion(s) within essential gene(s) into the vaccine/reagent phage(s), such that the phage can only form mature phage particles in a special fusion-cell that will conditionally permit its growth. These cells lack any homology to the phage outside of the conditionally expressible gene, so that marker rescue recombination of the wild type gene by the infecting phage defective for that gene is eliminated. The expression of the gene of interest is tightly regulated by a temperature sensitive lambda repressor, where the expression of the gene of interest is fully repressed at 30° C. and fully induced between 39-42° C. Examples of deletions or inactivated phage functions include but are by no means limited to: gene of interest-fusion cell, where the gene of interest can be one of the lambda genes J, V, W, Fll, A, Nul, E, D, or D+E involved in phage capsid formation, or lambda genes O, or P required for phage replication.

5.) Express the gene of interest in cells with special plasmids where expression of the gene of interest from the plasmid is regulated by a temperature sensitive repressor, i.e., is fully repressed in cells grown at 30° C. and fully induced upon moving the cells to 39-42° C.

5a) Incorporate an engineered deletion(s) within essential gene(s) into the vaccine/reagent phage(s), such that the phage can only form mature phage particles in a special fusion-cell that will conditionally permit its growth. These cells lack any homology to the phage outside of the conditionally expressible gene, so that marker rescue recombination of the wild type gene by the infecting phage defective for that gene is eliminated. The expression of the gene of interest is tightly regulated by a temperature sensitive lambda repressor, where the expression of the gene of interest is fully repressed at 30° C. and fully induced between 39-42° C. Examples of deletions or inactivated phage functions include but are by no means limited to: gene of interest-fusion cell, where the gene of interest can be one of the lambda genes J, V, W, Fll, A, Nul, E, D, or D+E involved in phage capsid formation, or lambda genes O, or P required for phage replication.

In another embodiment, a specific peptide sequence of interest is fused to D. In these embodiments, the gene fusions can be introduced to N- or C-terminal ends of D, which is within the bacterial chromosome and positioned just downstream from a powerful, highly regulatable promoter, for example, pR of lambda (SEQ ID No. 2), shown in FIG. 2. A perfect Shine-Delgarno ribosomal binding sequence (SEQ ID No. 4) was engineered just upstream of the AUG start for D expression and downstream from the start site for pR. The sequence is shown in FIG. 4

Referring to FIG. 5, this sequence shows oR2/oR1/pR (with imbedded pR promoter) regulatory region designed to place gene D (first four codons shown) at site of lambda gene cro. All of the indicated restriction sequences (XbaI, EcoRV, AvaI/SmlI/XhoI/TliI, BstYI/BamHI, and SpeI were engineered by the inventor. Cloning at the BamHI site permits exact replacement of gene D with a gene of interest (or adding an N-terminal addition to D between the BamHI and SpeI sites). As will be appreciated by one of skill in the art, this is a highly surprising and significant result in that the inventor has managed to mutate a Shine-Delgarno sequence, such that a highly useful restriction enzyme site has been created which allows direct cloning in frame downstream of a strong ribosome binding site. As discussed herein, in preferred embodiments, this sequence is incorporated into the lambda pR promoter, allowing for temperature-sensitive expression of a transcript including a strong ribosome binding site with a convenient restriction enzyme site for subcloning, as discussed herein.

The expression of D or the D::fusion from promoter pR is fully repressible or fully inducible, depending upon cellular temperature. Transcription from pR is completely prevented by the prophage Cl repressor binding to the operator OR sequences at 30° C. inhibiting transcription from the overlapping pR sequence. Partial inactivation of Cl[Ts] upon raising cells to 34° C. enables some transcription from pR, which becomes constitutive in cells placed above 38° C. Specifically, there is no expression from the pR promoter at 30° C., trace expression at 34-35° C., some expression at 37° C., higher expression at 38° C. and fully de-repressed expression from 39-42° C. Alternative highly regulatable, inducible promoters could be substituted for pR if needed. For example, transcription from the pBAD promoter for the arabinose operon in *E. coli* is fully repressed until arabinose is added to the medium, whereupon transcription becomes fully induced. pBAD, or similar promoters could be substituted for pR if there is a need to eliminate temperature regulation as the mechanism for gene induction. We have done this using two other strategies for making the plasmids: pB-pR-GOI-timm (where the Cl[Ts] repressor was deleted) or plasmid p434'-pR-GOI-timm (where the lambda operator and pR promoter were replaced by phage 434 rightward operator and pR promoter sequence). In pB-pR-GOI-timm the expression from, pR is constitutive. In p434'-pR-GOI-timm expression from pR is either constitutive, or can be regulated by 434 Cl[Ts] repressor.

Placing the D fusion construct on the bacterial chromosome has several advantages, as discussed herein. In essence, the D gene of phage lambda was inserted immediately downstream of the strong pR promoter present on a defective prophage (23) within the *E. coli* chromosome, replacing the prophage regulatory and replication genes cro-ren. D expression is fully repressed in a D-cell by a temperature sensitive [Ts] Cl repressor protein (encoded by the defective prophage). The Cl repressor binds to OR at 30° C. preventing transcription from the overlapping pR sequence. Partial inactivation of Cl[Ts] upon raising cells to 34° C. enables some transcription from pR, which becomes constitutive in cells placed above 38° C. The efficiency of plating (eop) of the D-cell is the same (1.0) between 30-37° C., drops to 0.73 at 39-40° C., 0.56 at 42° C. and is less than 0.1 above 44° C., indicating that the cells tolerate massive expression of D and the accumulation of D protein. The D-cell was made such that not one base of DNA sequence straddling D (as situated on the lambda genome) was placed downstream of pR in the defective prophage within the cell chromosome. Therefore, the chance is virtually nil that the D fusion can rescue an intact D gene from the chromosome of a D-cell or D-insertion-cell.

Thus, by varying temperature, the amount of intact D provided for phage particle assembly can be varied so that phage assembly can be maximized. That is, as discussed above, D can tolerate variable N- or C-terminal additions, but fusion additions encoding very large proteins/polypeptides can impact the ability of D to assemble into phage particles due to steric concerns, that is, the fusion peptide, depending on the size and/or shape, could obstruct decoration of the head. In addition, as discussed above, in some embodiments, it may be desirable to regulate the number of copies of the fusion peptide presented on each phage head when detecting high affinity interactions. However, supplying intact D in trans under the control of an inducible promoter provides an elegant method for easily maximizing transgenic phage particle production by simply varying temperature, as discussed above.

For example, the lambda display particle displaying the gene of interest expression product can be used as a diagnostic or as a therapeutic. In some embodiments, for example, the fusion phages are used in effect as substitutes for passive immunity. As discussed above, in phage therapy, phages can be administered via subcutaneous, oral, nasal and/or intramuscular routes. Absorbed phages rapidly circulate throughout the tissues and are eventually removed by the spleen, liver and other filtering organs of the reticuloendothelial system.

In other embodiments, the gene of interest fusion constructs are engineered to include an 'affinity handle', that is, a domain or 'tag' which can be used to isolate and further purify the library member and its bound target. Suitable tags are well-known to those of skill in the art; however, constructions have been prepared which comprise three modified FLAG sequences and the calmodulin binding peptide (CBP). FLAG and CBP react with two different high affinity binding peptides which in turn permits extremely high level, two step purification of the expressed protein and any attached cellular protein. The cellular protein can then be identified as bands on a protein gel and submitted for sequencing, for example, for MALDI-TOFMS analysis.

As discussed herein, this system provides a safe and efficient means for generating phage particles expressing a library of small peptide fusion-additions to D or for generating large amounts of phage particles presenting a specific D-fusion.

As will be appreciated by one of skill in the art, the safety and efficiency of the system described herein can be customized and modified by modifications of the expression system and the expression host cell. As used in this context, 'efficiency' does not simply refer to 'high expression' but rather 'expression of the desired construct'.

As discussed above, the D-fusions may be supplied in trans from the expression host chromosome under the control of either a constitutive or inducible promoter. In these embodiments, the lambda particles will be coated with D-fusions displaying the expression product of the gene of interest or displaying the library fusion products but the phage genome within the phage head will not encode the D-fusion. In these embodiments, as discussed above, wild-type D may also be supplied in trans under the control of an inducible promoter, thereby providing a quick and easy method for maximizing phage head assembly conditions by simply varying conditions of promoter induction. For example, when the inducible promoter is pR, varying temperature may be used.

For example, as discussed above, the lambda assembly vectors may include safety features to prevent multiplication of the phage within the natural environment. For example, the assembly vectors may be devoid of antibiotic resistance markers and may not use any commercially-available plasmids or phages.

More preferably, the lambda vectors lack the immunity region (cl-rex) and thus cannot lysogenize infected cells. The lambda vectors may also be deleted for the nin5 recombination region. The lambda vectors preferably include the gene gam so that it protects linear concatemeric-packagable DNA formed via rolling circle replication.

For use, suitable phage particles as described herein may be prepared by a variety of means, depending of course on their intended use.

For example, in some embodiments [preparing LDP-cells, LDNAP-cells, and L2DP cells], the suitable bacterial cell comprises a thermally inducible heteroimmune lambdoid phage that is defective for cell lysis and phage burst. Upon thermal inactivation of the phage repressors the prophage is induced as is expression of complementing or phage coating proteins or both. Because the induced prophage cannot lyse the cells, hundreds of copies of mature, coated phage particles collect within the cells. The phage particles are then recovered, for example, by concentrating the cells by pelleting and then killing the cells with an agent used to prepare killed vaccines. In some embodiments, the entire cells are used as vaccines although in other embodiments, the phage particles may be further purified. When introduced into the gut, the cells are taken up and lysed, releasing the LDP immunogens.

In other embodiments [preparing LDP-exclusion cells, LDNAP-exclusion cells, and L2DP-exclusion cells], the prophage within the suitable host cell is not only incapable of lysing the cells, the prophage is also engineered to carry a different host range (or a defective tail fiber gene nullifying phage attachment to cells), for example, a different cell attachment mechanism, so that when the cells are lysed or otherwise 'broken', the released mature particles cannot and do not bind to any of the cells and/or cell wall components present in the culture. As will be appreciated by one of skill in the art, as a result of this arrangement, this permits highly efficient separation of phage particles from the debris, for example, by cell pelleting, external cell lysis, isopycnic gradient centrifugation as well as other suitable means known in the art.

As will be appreciated by one of skill in the art, the release of genetically modified organisms is a cause for considerable concern. However, as discussed herein, the power of lambda genetics allows for numerous safety features to be incorporated into the system, thereby providing a highly flexible and powerful system for the construction of therapeutic and diagnostic recombinant lambda phage particles.

Several unique, or safety advantages of the phage display cell system include but are by no means limited to: i) controlling or exclusively directing D-fusion protein incorporation into the phage particle; ii) the displayed peptide/polypeptide is not encoded within the genome of the display phage; iii) the phage display particle is not naturally viable and can only grow in special cells complementing defective essential phage functions; and iv) the cell system provides a new approach for fusing random oligonucleotides used to make a random phage library, and for screening peptide binding affinity.

Specifically, in one embodiment of the particle preparation process an engineered lambda phage particle comprising a peptide of interest can be fused to either the C-terminus or N-terminus of the lambda D gene. As a result of this arrangement, up to 405-420 copies of the D-fusion proteins per particle or per phage head can be displayed. Specifically, fusion to the C-terminus or N-terminus does not interfere with the interaction of D monomers to form a trimer or with the incorporation of these trimers into the lambda capsid or head.

The number of D-fusions present on a lambda phage head is often referred to as the 'display density' when D-fusions are used in phage display systems. Very low display densities can enable the isolation of binders with very high affinity for a ligand, intermediate display densities allow the isolation of binders where the strength of interaction is the nanomolar to micromolar range, and display densities on the order of a hundred or more are needed for weaker (micromolar to millimolar) interactions. In addition, the peptides displayed can range from about 10 to several hundred amino acids. As will be appreciated by one of skill in the art, these estimates are intended to illustrate that both the display density as well as the displayed peptide size can by substantially varied. The system described herein permits the lambda display density to be varied by changing the culture temperature between 25° and 44° C.

In one embodiment of the invention, a library of nucleotide sequences encoding short peptide sequences are fused in frame to the D gene. In these embodiments, small peptides of about 5-15 residues, for example, about 10 residues are displayed within the context of D at 405-420 copies per lambda phage particle. Preferably, the small peptides are inserted proximal to the N-terminal end of D.

In a preferred embodiment, recombineering technology is utilized. For example, $E.$ $coli$ lysogens of lambda c[Ts]857 will be transiently induced at 42° C. for 5 minutes to express exo-bet-gam, returned to 30° C. and then transformed, for example, by electroporation, with single strand DNA oligonucleoties comprising random nucleotides placed between flanking base sequences that both precede and follow the N-terminal AUG for D, that is, the insertion site, as situated on the intact phage. This permits the fusion of the amino acids, that is, the library of small peptides, at the N-terminal end of D, for example, between the AUG and the second codon. Following electroporation, the cells will be transiently grown at 30° C. to permit the formation of the N-terminal D recombinants. Subsequently, the cells will be shifted to nonpermissive temperature to induce the lambda cl[Ts] 857 or lambda clTs]857D::fusion prophages. We typically obtain phage lysates with titers of $2\times10^9$ phage particles per ml from induced lambda.cl[Ts]857 lysogens.

As will be appreciated by one of skill in the art, in these embodiments, the flanking sequences must be of sufficient length to initiate a recombination event, as discussed herein. For example, the flanking sequences may be 35 base homologies at either end.

In an alternative embodiment, the short peptides are fused to D at the C-terminal end of D. As will be appreciated by one of skill in the art, the fusion library will then be expressed 'downstream' of D, meaning that less care is necessary to ensure that the insertion sequences are in frame and lack termination codons.

As will be appreciated by one of skill in the art, other suitable methods for the generation of the phage library may be employed as may other methods for the detection of insertion or recombination events. For example, random insertions between the BamHI and SpeI restriction sites within plasmid pclpR-D-timm, followed by removal of the pR-N-addition-D-timm sequence an cloning between the BsiWI and EcoRI sites in one of the LDNAP phage vectors. However, one advantage of the D-cell-recombineering method described above is that the phage display library can be utilized without further manipulation.

Thus, in these embodiments, a phage lysate is grown of all the different cloned products, representing millions of D-fusion variant phage particles. Using the above analogy where the target molecule is bound to a bead, the reacted beads would be washed, mixed with sensitive cells, and plaques identified by mixing the beads with sensitive host cells, This will enable plaque-purification of a rare phage that displays the unique binding (affinity) properties for which we are searching. Once a plaque-purified high affinity phage is purified we will be able to amplify the "D::unique-polypeptide" genetic information by plaque-PCR, and then introduce the fragment into a D-minus-cell, creating a D-fusion-recombinant cell. The D-minus cell includes an 11 base pair all-STOP sequence (termination codons in all three reading frames for the coding strand) is positioned within the first few codons after the AUG for start of D. The D-fusion recombinant cell can be selected by its ability to support the plating of a lambda D null mutant phage.

Lytic phage display permits construction of large molecular libraries of variants and selection techniques that allow efficient searches of the library without testing each member when the displayed peptide/polypeptide is encoded within the display phage genome. In essence these phages have two interactive ends: the fusion polypeptide is displayed on the phage head, whereas the phage tail tip permits the injection of phage into sensitive bacterium. A fusion phage(s) displaying a polypeptide is selected on the basis of its affinity to a target molecule (assume bound to a magnetic bead). The beads are washed and mixed with sensitive bacteria, which are infected upon attachment of the phage tail tip to the cells, allowing selection of a very unique binder phage from libraries of $10^{10}$ or greater phage particles. Each unique resulting phage plaque encodes the D::fusion genetic information displayed as a D-peptide on the phage head of the phage that bound to the immobilized target molecule. In one embodiment, the method for producing N-terminal D-fusions starting with D-minus-cells creates $E.$ $coli$ cells capable of displaying by leaching D. Alternatively, the cells can be infected and an infecting phage that does not itself encode a D::fusion will have D displayed on the head of the phage bursting from the lysed cells. Either cells displaying a unique D or phage coated with D can be selected.

In other embodiments, the fusion library constructs are engineered to include an 'affinity handle', that is, a domain or 'tag' which can be used to isolate and further purify the library member and its bound target. Suitable tags are well-known to those of skill in the art; however, constructions have been prepared which comprise three modified FLAG sequences and the calmodulin binding peptide (CBP). FLAG and CBP react with two different high affinity binding peptides which in turn permits extremely high level, two step purification.

The sequence includes lambda operator sites oR2 and oRI for regulation of the pR promoter by a temperature sensitive cl repressor present in cryptic prophage. The pR promoter drives the transcription of codon optimized lambda gene D positioned exactly as is gene cro in phage lambda. Gene D sequence was codon optimized for expression in $E.$ $coli$ by modification of 51 of the 110 codons.

Gene D is fused at the carboxy-terminal end with a flexible GGSGA (gly-gly-ser-gly-ala) linker sequence into which were designed the AscI/SgsI and BssHI restriction sites and four sections (presumptive epitopes) of the capsid gene from porcine circovirus 2 (PCV2).

The sequence for the four regions of the PCV capsid gene, i.e., for amino acids 65-87, 113-146, 158-183, and 194-207 were joined using the linker AAY (ala-ala-tyr) that has been used in DNA string technology, rather than the more common linker GGS (gly-gly-ser). In AAY (Ala-Ala-Tyr), the DNA sequences used for optimum codons were gcg (28%) for Ala and tat (19%) for tyrosine.

The PCV2 capsid sequence information was from GeneBank sequence DQ629119 of PCV2, determined the most representative of 10 sequences analyzed. A unique BamHI site was designed into the sequence including the consensus SD (Shine-Delgarno) sequence [aggagg] as for lambda gene cro. This permits either the placement of N-terminal fusions a gene D, or the entire replacement of gene D.

A powerful Rho-independent (self-) terminator sequence was placed downstream of D-CAP in order to prevent transcription from the strong pR promoter from transcribing into adjacent sequences into the replication vector into which the pR-D-CAP or pR-D-GOI, or pR-GOI sequence is placed. Several strategic modifications were introduced into the naturally occurring timm terminator downstream of gene rexB in lambda in order to place AvaI-SmaI/XmaI restriction sites. This promoter effectively blocks about 150-fold increase of Cl-rexA-rexB transcription arising from promoter pRE (in absence of Cro activity) so that it does not read-through into leftward pL-N promoter.

While the preferred embodiments of the invention have been described above, it will be recognized and understood that various modifications may be made therein, and the appended claims are intended to cover all such modifications which may fall within the spirit and scope of the invention.

The invention claimed is:

1. A method of preparing a lambda phage particle comprising:

providing a permissive host bacterial cell comprising an expression system comprising a nucleic acid molecule comprising lambda pR promoter consisting of the nucleotide sequence as set forth in SEQ ID NO:2 and operably linked to a nucleic acid molecule encoding a Shine-Delgarno sequence consisting of the nucleotide sequence as set forth in SEQ ID NO:4 and operably linked to a nucleic acid molecule encoding lambdaphage D gene consisting of the nucleotide sequence as set forth in SEQ ID NO:1, said lambdaphage D gene sequence comprising inserted in frame with the lambdaphage D gene a nucleic acid molecule encoding a gene of interest, said permissive host bacterial cell being suitable for vegetative growth of lambdaphage and further comprising the cI$^{TS}$857 repressor;

subjecting the host bacterial cell to conditions such that bacteriophage particle expression and assembly is initiated; and recovering the bacteriophage particles from the culture, thereby providing a lambda phage particle.

2. The method according to claim 1 wherein a plurality of cultures of said permissive host bacterial cell are grown, each respective culture is grown at a temperature between 25-44° C.; and the number of phage particles produced in each respective culture is determined, thereby determining the optimal temperature for phage assembly of a recombinant lambda phage particle displaying the gene of interest.

3. The method according to claim 1 wherein the gene of interest is operably linked to a modified Rho-independent mRNA termination signal timm consisting of the nucleotide sequence as set forth in SEQ ID NO:7.

4. The method according to claim 1 wherein the gene of interest is porcine circovirus 2 capsid protein-derived sequence consisting of the nucleotide sequence as set forth in SEQ ID NO:3.

5. A method of preparing a lambda phage particle comprising:

providing a permissive host bacterial cell comprising a lambda prophage lacking a functioning copy of at least one essential lambdaphage gene and an expression system comprising a nucleic acid molecule comprising lambda pR promoter consisting of the nucleotide sequence as set forth in SEQ ID NO:2 and operably linked to a nucleic acid molecule encoding a Shine-Delgarno sequence consisting of the nucleotide sequence as set forth in SEQ ID NO:4 and operably linked to a nucleic acid molecule encoding lambdaphage D gene consisting of the nucleotide sequence as set forth in SEQ ID NO:1, said lambdaphage D gene sequence comprising inserted in frame with the lambdaphage D gene a nucleic acid molecule encoding a gene of interest, said permissive host bacterial cell being suitable for vegetative growth of lambdaphage and further comprising the $cI^{TS}857$ repressor;

subjecting the host bacterial cell to conditions such that bacteriophage particle expression and assembly is initiated; and recovering the bacteriophage particles from the culture, thereby providing a lambda phage particle, wherein the lambdaphage particles recovered from the culture are lacking a functioning copy of at least one essential lambdaphage gene.

* * * * *